United States Patent
Zheng et al.

(10) Patent No.: US 10,874,469 B2
(45) Date of Patent: Dec. 29, 2020

(54) REMOTELY OPERATED ORTHOPEDIC SURGICAL ROBOT SYSTEM FOR FRACTURE REDUCTION WITH VISUAL-SERVO CONTROL METHOD

(71) Applicant: Tsinghua University, Beijing (CN)

(72) Inventors: Gangtie Zheng, Beijing (CN); Shijie Zhu, Beijing (CN); Yu Chen, Beijing (CN); Bicong Zhang, Beijing (CN); Yongwei Pan, Beijing (CN); Zhe Zhao, Beijing (CN); Jiuzheng Deng, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 302 days.

(21) Appl. No.: 16/138,889

(22) Filed: Sep. 21, 2018

(65) Prior Publication Data
US 2019/0125461 A1    May 2, 2019

(30) Foreign Application Priority Data

Oct. 27, 2017 (CN) ............................ 2017 1 0361356
Nov. 10, 2017 (CN) ............................ 2017 1 1102592

(51) Int. Cl.
*G06F 17/00* (2019.01)
*A61B 34/37* (2016.01)
(Continued)

(52) U.S. Cl.
CPC ............ *A61B 34/37* (2016.02); *A61B 17/808* (2013.01); *A61B 17/8866* (2013.01);
(Continued)

(58) Field of Classification Search
CPC ......... A61B 34/37; A61B 34/10; A61B 34/35; A61B 90/14; A61B 90/37; A61B 17/808;
(Continued)

(56) References Cited

U.S. PATENT DOCUMENTS

| | | | |
|---|---|---|---|
| 5,971,984 A * | 10/1999 | Taylor | A61B 17/62 128/898 |
| 6,387,100 B1 * | 5/2002 | Lindequist | A61B 6/12 606/88 |

(Continued)

OTHER PUBLICATIONS

Du, Hong et al. "Advancing computer-assisted orthopaedic surgery using a hexapod device for closed diaphyseal fracture reduction", Int J Med Robotics Comput Assist Surg 2015; 11:348-359.
(Continued)

*Primary Examiner* — Ronnie M Mancho
(74) *Attorney, Agent, or Firm* — Loza & Loza, LLP; Michael F. Fedrick

(57) ABSTRACT

A remotely operated orthopedic surgical robot system for performing a fracture reduction operation using a visual-servo control method is provided. The system includes the surgical image acquisition equipment, the fracture reduction robot and the remote operation workstation. The fracture reduction robot has a plurality of types. The remote operation workstation includes a graphical user interface for doctors to examine the fracture reduction path planning result made by an artificial intelligence algorithm and to manually perform the path planning. The remote operation workstation calculates the robot control quantity using the visual servo control method according to the path planning result and sends it to the robot.

20 Claims, 6 Drawing Sheets

(51) Int. Cl.

| | | |
|---|---|---|
| *A61B 90/14* | (2016.01) | |
| *A61B 17/88* | (2006.01) | |
| *A61B 17/80* | (2006.01) | |
| *G06N 3/08* | (2006.01) | |
| *G16H 20/30* | (2018.01) | |
| *A61B 90/00* | (2016.01) | |
| *A61B 34/10* | (2016.01) | |
| *A61B 34/35* | (2016.01) | |
| *A61B 17/56* | (2006.01) | |
| *A61B 34/00* | (2016.01) | |
| *A61B 34/30* | (2016.01) | |
| *A61B 17/00* | (2006.01) | |
| *A61B 17/68* | (2006.01) | |

(52) U.S. Cl.
CPC .............. *A61B 34/10* (2016.02); *A61B 34/35* (2016.02); *A61B 90/14* (2016.02); *A61B 90/37* (2016.02); *G06N 3/08* (2013.01); *G16H 20/30* (2018.01); *A61B 34/25* (2016.02); *A61B 2017/00022* (2013.01); *A61B 2017/00123* (2013.01); *A61B 2017/00199* (2013.01); *A61B 2017/564* (2013.01); *A61B 2017/681* (2013.01); *A61B 2034/107* (2016.02); *A61B 2034/304* (2016.02); *A61B 2090/064* (2016.02); *A61B 2090/364* (2016.02); *A61B 2090/376* (2016.02); *A61B 2090/3764* (2016.02)

(58) Field of Classification Search
CPC .......... A61B 17/8866; A61B 2034/107; A61B 34/25; A61B 2034/304; A61B 2090/064; A61B 2090/364; A61B 2090/376; A61B 2090/3764; A61B 2017/00022; A61B 2017/00123; A61B 2017/00199; A61B 2017/564; A61B 2017/681; G16H 20/30; G06N 3/08
USPC .......................................................... 700/245
See application file for complete search history.

(56) References Cited

U.S. PATENT DOCUMENTS

| | | | |
|---|---|---|---|
| 7,413,565 B2 | 8/2008 | Wang et al. | |
| 9,610,101 B2 | 4/2017 | Tang | |
| 9,718,190 B2* | 8/2017 | Larkin | A61B 90/37 |
| 9,775,681 B2* | 10/2017 | Quaid | G06F 19/00 |
| 10,028,789 B2* | 7/2018 | Quaid | A61B 34/30 |
| 10,568,704 B2* | 2/2020 | Savall | A47B 21/03 |
| 2004/0254771 A1* | 12/2004 | Riener | G09B 23/32 |
| | | | 703/7 |
| 2010/0234844 A1* | 9/2010 | Edelhauser | A61B 17/62 |
| | | | 606/56 |
| 2010/0331858 A1* | 12/2010 | Simaan | A61B 34/37 |
| | | | 606/130 |
| 2011/0238079 A1 | 9/2011 | Hannaford et al. | |
| 2014/0379038 A1* | 12/2014 | Dogramadzi | A61B 17/62 |
| | | | 606/86 R |
| 2017/0027803 A1* | 2/2017 | Agrawal | A61B 5/224 |
| 2018/0092757 A1* | 4/2018 | Behzadi | A61F 2/367 |

OTHER PUBLICATIONS

Lebret, G. et al. "Dynamic Analysis and Control of a Stewart Platform Manipulator", Automation & Robotics Research Institute, 1992, pp. 629-655.

Westphal, Ralf et al. "Robot-assisted Long Bone Fracture Reduction", The International Journal of Robotics Research, vol. 28, No. 10, Oct. 2009, pp. 1259-1278.

Goodfellow et al., Deep Learning, MIT Press, 2016.

François Chaumette, S. Hutchinson, Visual servo control, Part I: Basic approaches, IEEE Robotics and Automation Magazine, Institute of Electrical and Electronics Engineers, 2006, 13(4):82-90.

Westphal R., et al., Robot-assisted long bone fracture reduction, International Journal of Robotics Research, 2009, 28(10):1259-1278.

Du H., Hu L., Li C., et al. Advancing computer-assisted orthopaedic surgery using a hexapod device for closed diaphyseal fracture reduction. International Journal of Medical Robotics + Computer Assisted Surgery, 2014, 11(3):348-359.

* cited by examiner

REMOTELY OPERATED ORTHOPEDIC SURGICAL ROBOT SYSTEM FOR FRACTURE REDUCTION WITH VISUAL-SERVO CONTROL METHOD

CROSS-REFERENCE TO RELATED APPLICATIONS

This application claims the benefit of priority under 35 U.S.C. § 119 from Chinese Patent Application No. 201710361356.1, filed Oct. 27, 2017, and from Chinese Patent Application No. 201711102592.8, filed Nov. 10, 2017. The disclosures of the foregoing applications are incorporated herein by reference in their entirety.

FIELD OF THE INVENTION

The present invention relates to the field of orthopedic surgical robots, especially for fracture reduction remotely controlled with a control method based on a visual-servo control method.

BACKGROUND OF THE INVENTION

Minimal invasive technology is widely used in traumatic fracture reduction and fixation operations, which however raises a problem that doctors have to perform these surgeries under X-ray radiation. For complicated fracture surgeries, extensive X-ray exposure is usually inevitable, which is a threat to doctors' health. Thus, a remotely operated orthopedic surgical robot system is needed.

The operation of current orthopedic surgical robots relies on coordinates provided by special surgical navigation technologies including CT, X-ray images and infrared optical tracking systems. These surgical navigation technologies are based on absolute coordinates in physical space. In other words, the function of the navigation system is to acquire the position and the pose of the surgery tools and the surgical site described in the same absolute coordinate system, namely the registration procedure. (Court-Brown, C. M., Heckman, J. D., McQueen, M. M., Ricci, W. M. & Tornetta, P. Rockwood and Green's fractures in adults. 8 edn, Lippincott Williams & Wilkins, 2015). Then the surgical robot operates according to this position and pose information.

There are three drawbacks of these navigation methods. Firstly, a time consuming preoperative calibration of the image acquisition equipment is needed, which may cause accuracy loss of the system due to calibration errors. Secondly, necessary trackers mounted on the surgical tools and the patient's body lead to extra injuries to the patient and additional surgery steps. Thirdly, the purchase of customized navigation systems, such as intraoperative computed tomography (CT) and infrared optical navigation systems, means an increase of the surgery cost.

Moreover, most of the current surgical robots are based on open-looped control. Specifically, before the operation, the navigation system is used to obtain the position information of the robot manipulator, the surgical site, or the limb held by the manipulator in an absolute coordinate system. According to thus-obtained information, the robot's motion trajectory is then calculated and the robot moves following a preplanned trajectory in the operation. In short, it can be summarized as "preoperative planning—intraoperative execution", or in the other words, the robot can only perform tasks mechanically and does not have the ability to make real time adjustments during the operation. As a matter of fact, the errors in the preoperative planning, the deformation of optical trackers, and even the movement of the surgical site caused by the patient's breathing could greatly reduce the accuracy of the operation and even lead to a failed surgery. For example, the fracture reduction robot proposed in Du, et al. (Du H., Hu L., Li C., et al. Advancing computer-assisted orthopedic surgery using a hexapod device for closed diaphyseal fracture reduction. International Journal of Medical Robotics+Computer Assisted Surgery, 2014, 11(3): 348-359) is based on the "preoperative planning—intraoperative execution" control strategy, in which the robot moves along the trajectory calculated preoperatively according to the CT information and cannot make real time feedback through the visual information.

Though intraoperative real time feedback methods are used in some of the surgical robots, all of them are based on indirect methods like infrared optical tracking instead of direct image information. For example, in the fracture reduction and intramedullary nailing robot system proposed in Westphal, et al. (Westphal R., Winkelbach S., Wahl F., et al. Robot-assisted long bone fracture reduction. International Journal of Robotics Research, 2009, 28(10): 1259-1278), preoperative CT and X-ray images are used to make a surgery plan, and an intraoperative infrared optical tracking device is used for feedback (infrared markers are mounted on the bones). However, as X-ray images are not utilized during the surgery, the reduction accuracy is likely to be influenced by the muscle's flexibility and tension, and hence by consequent optical marker displacement. To cope with this problem, the patient's limb is usually fixed on the robot's working platform with steel pins through the bones, as described in U.S. Pat. No. 9,610,101 to Tang, et al. Extra injuries to the patient are unavoidable in this method.

In recent years, visual servo has received more and more attention in the field of robotics. The so-called visual servo method, that is, to obtain the target and the robot's position or motion information through a visual sensor, is used in real time for robot motion control to guide a robot to complete a specific task, as discussed in Chaumetee, et al. (Francois Chaumetee and Seth Hutchinson, Visual servo control Part I: Basic approaches, IEEE Robotics & Automation Magazine, December 2006, 82-90). In the visual servo framework, a closed-loop control based on visual feedback is used, and the positioning accuracy of the robots is higher than that of the open-loop control. With the help of visual servo technology, robots can make adjustments to target movement that may occur in practice. Moreover, a branch of the visual servo technology, namely "image-based calibration-free visual servo" technology, avoids the calibration steps in the traditional visual servo by introducing the concept of relative coordinates, which greatly simplifies the preparation process. On the other hand, with the development of digital image processing technology, instead of heavily relying on visual markers mounted on the target or the robot end-effector, it is feasible to control the robot directly using the image features of the targets and the robot's end-effector. However, visual servo technology hasn't yet been applied in the field of surgical robots.

The effectiveness and efficiency of fracture reduction rely on an appropriate reduction strategy and path planning method. Although significant advances have been made in artificial intelligence technology, it is still not competent for complicated fractures and incomplete information. In addition, in order to ensure security, the reduction strategy and path plan given by an artificial intelligence algorithm also need to be examined by a doctor. Therefore, an interactive interface between doctors and the surgical robot system is necessary for doctors to make a path plan and validate the results of the artificial intelligence algorithm.

SUMMARY OF THE INVENTION

The purpose of the proposed invention is to overcome the deficiencies of the prior technologies and provide a remotely operated orthopedic surgical robot system for fracture reduction and a reduction control method based on the visual servo technology. This visual servo control method only relies on the G-arm or C-arm X-ray machines commonly used in the operation room for closed-loop control, eliminating complicated registration procedures and incidental optical markers that bring extra injuries and pain to patients. And for the reduction of long bone fractures, it is no longer necessary to use steel pins to fix the patient's broken limbs to the robot's end-effector. The proposed graphical user interface allows doctors to perform manual fracture reduction path planning or validate the path plan given by an artificial intelligence algorithm. In this way, we provide a new way for doctors to interactive with the robots. In brief, the doctor assigns desired new positions of a bone fragment in the image (either pushing buttons as described in the embodiments or by drawing a line with a mouse). This is different from any published research. The proposed robot system has the merits of simple composition, clear and intuitive usage, and suitable for a plurality of complicated fractures.

The present invention provides a reduction control method based on the system as described above, characterized in that the patient's fractured part of the body is fixed flexibly to the robot's end effector, i.e. small relative motion between the body and the robot's end effector is allowable. The operation procedures are preferably as follows:

1) The surgical image acquisition equipment acquires two real-time images, an anteroposterior (AP) view and a lateral (LT) view, which are sent to the remote operation workstation with data line or wireless network, then the images are shown on the graphical user interface on the said workstation.
2) The artificial intelligence algorithm first processes the image, including edge extraction, midline extraction, path planning, and reduction position display. Then according to the above information shown on the graphical user interface, the doctor judges whether the results of edge extraction, midline extraction and path planning are appropriate. If there are some problems, then the results given by the artificial intelligence algorithm are deleted and the doctor manually draws the midlines (or adjusts the bone edges) and makes the path planning
3) In the manual mode, the operator decides whether the fracture reduction needs to continue according to the AP and LT images displayed on the graphical user interface or according to whether the absolute value of the reduction error w is smaller than a predefined value: if it is not necessary to continue, the reduction procedure is completed; otherwise, the operator (usually a doctor) makes the path planning through the graphical user interface by clicking the corresponding buttons, and after confirming in the graphical user interface that the robot will not exceed its working space after the movement, the operator clicks the "Run" button and the control error e is calculated.
4) With the control error e calculated as in 3), according to the image-based calibration-free visual servo control law, the correspondent control quantity r of the robot is as follows:

$$r = J^{\dagger}\left(-k_P e - k_I \int e\,dt - k_d \frac{de}{dt}\right)$$

wherein r is a vector representing the variation of the position and orientation of the robot end effector, or a vector that represents the variation of the lengths of the linear actuators or the angles of the joints of the robot; $k_P$, $k_I$, $k_D$ are the proportional coefficient, integral coefficient and differential coefficient respectively; J is the Jacobian matrix; $\int e\,dt$ is the integration of control error e over time t, $$\frac{de}{dt}$$

is the derivative of the control error e to time t.

5) The control quantity r is the command for instructing the robot's motion that is sent to the fracture reduction robot by the said workstation. After the robot's movement, the operation procedure returns to step 1). The control quantity r includes three cases depending on what kind of robot is used:
   a) r is a vector representing the variation of the position and orientation of the robot end effector. In this case x is the vector representing the current position and orientation of the robot, and then the robot moves to x+r, which represents its new position and orientation;
   b) r is a vector representing the variation of the lengths of the linear actuators of the robot. In this case l is the vector representing the current lengths of the linear actuators of the robot, and then the linear actuators of the robot change their lengths to l+r; or
   c) r is a vector representing the variation of the angles of the joints of the robot. In this case, θ is the vector representing the current angles of the joints of the robot, and then the joints rotate to a new angle represented by θ+r.
6) In step 5), a force sensor, which is installed between the robot's end-effector and the injured body part's fixator, measures the force change rate during the robot movement. If there is a sudden increase of the force detected by the force sensor, indicating contact between the bone segments, the control system will stop the robot and activate an alarm automatically. The doctor then examines the X-ray images and decides whether the reduction is completed. If completed, then the operation is stopped, otherwise the process returns to step 2) or 3) to redo the path planning.

In step 4), the control error e is calculated as follows:

$$e = [\Delta x_1\ \Delta y_1\ \Delta \theta_1\ \Delta x_2\ \Delta y_2\ \Delta \theta_2\ \alpha]^T$$

wherein $\Delta x_1$, $\Delta y_1$, $\Delta \theta_1$ are the horizontal displacement, the vertical displacement, and the rotation angle of the contour line of the distal bone segment after the robot's movement with respect to the mark line, which represents the midline of the distal bone segment after the robot's movement, in the AP fluoroscopy image generated by the doctor through the graphical user interface. $\Delta x_2$, $\Delta y_2$, $\Delta \theta_3$ are the horizontal displacement, the vertical displacement and the rotation angle of the contour line of the distal bone segment after the robot's movement with respect to the mark line, which represents the midline of the distal bone segment after the robot's movement, in the LT Fluoroscopy image generated by the doctor's operation through the graphical user interface. α represents the angle of the double arrow, which represents the rotation angle of the axis of the distal bone segment after the robot's movement, with respect to the vertical direction.

In step 3), the reduction error w is calculated as follows:

In the AP fluoroscopy image, let the angle between the horizontal direction and the mark line, which represents the midline of proximal bone segment, be $\theta_1$, and let the pixel coordinates of its endpoint close to the side of the fractured segment be $(x_1,y_1)$; and let the angle between the horizontal direction and the mark line, which represents the midline of the distal bone segment, be $\hat{\theta}_1$, and the pixel coordinates of its endpoint close to the side of the fractured segment be $(\hat{x}_1, \hat{y}_1)$. In the LT Fluoroscopy image, let the angle between the horizontal direction and the mark line, which represents the midline of the proximal bone segment, be $\theta_2$, and let the pixel coordinates of its endpoint close to the side of the fractured segment be $(x_2,y_2)$; and let the angle between the horizontal direction and the mark line, which represents the midline of distal bone segment, be $\hat{\theta}_2$, and let the pixel coordinates of its endpoint close to the side of the fractured segment be $(\hat{x}_2,\hat{y}_2)$. With these definitions, the reduction error w is given by the following:

$$w = \begin{bmatrix} \hat{x}_1 - x_1 \\ \hat{y}_1 - y_1 \\ \hat{\theta}_1 - \theta_1 \\ \hat{x}_2 - x_2 \\ \hat{y}_2 - y_2 \\ \hat{\theta}_2 - \theta_2 \end{bmatrix}$$

The criterion of reduction completion is w=0, which means the fracture is reduced anatomically.

The features and benefits of the present invention include:

1. The graphical user interface is clear and intuitive so that only a 2-D image based path planning is needed and it doesn't require the coordinate transformation from 2-D to 3-D, which is quite convenient for doctors. What's more, the present invention can cope with more complicated fractures than a fully automated fracture reduction robot system.
2. The present invention adopts a remote control method, that is, the operator can send instructions to the robot through the graphical user interface in a place far from the radiation area, and thereby completely avoid exposure to radiation. In addition, thanks to the remote control method, surgical experts can operate the surgical robots in other places far from the operation room, which helps to improve the healthcare condition of undeveloped and rural areas and save the time of the surgical experts on the way to the operation room.
3. The surgical robot system of the present invention adopts a "visual servo" control method, which can utilize visual information acquired during the surgery to feed back the robot's motion, which can effectively avoid the loss of accuracy in surgery caused by preoperative planning errors and movement of the surgical site during surgery. Compared to the traditional "preoperative planning—intraoperative execution" framework, the present method has better accuracy and is also more in line with doctors' clinical thinking and fracture reduction surgery habits.
4. The surgical navigation technology of the present invention adopts an "image-based calibration-free visual servo" technology, which avoids the installation and calibration of additional optical markers, and can effectively reduce the preparation time. This technology can also effectively reduce the errors caused by uncertainties such as displacement of the patient's surgical site and image acquisition equipment. It is also not necessary to rigidly fix an injured body part to a robot end-effector.
5. The surgical image acquisition system of the present invention makes use of surgical devices which are commonly used in operation rooms such as a G-arm or a C-arm X-ray machines, and does not require additional expensive equipment such as an intraoperative CT or infrared optical tracking system, which not only saves surgery costs but also reduces the time for training the medical personnel.

BRIEF DESCRIPTION OF THE DRAWINGS

The invention can be better understood and appreciated more fully through the following descriptions in combination with the accompanying drawings, wherein the same or similar reference numerals are used to represent the same or similar parts in all the accompanying drawings. The accompanying drawings, together with the following detailed description, are included in the specification, form one part of the specification and also used for further describing the preferred embodiments of the invention and explaining the principles and merits of the invention. In the drawings.

DETAILED DESCRIPTION OF THE PREFERRED EMBODIMENTS

Hereinafter, the exemplary embodiments of the invention are described in detail in combination with the accompanying drawings. For clarity and concision, the specification does not describe all the features of practical implementations. However, it should be understood that, in the process of developing any practical embodiments, many implementation-specific decisions must be made to achieve the specific targets of developers, for instance, to be in line with those limiting conditions that are related to a system and business, and these limiting conditions may change with the different implementations. It also has to be understood that although such development work may be complex and take long time, the development work is merely a routine task for those of skill in the art having the benefit of this disclosure.

Here, it should be noted that for preventing unnecessary details from obscuring the invention, only device structures, methods and processing steps that are closely related to the scheme according to the invention are illustrated in the accompanying drawings and description, and the representations and the descriptions of parts, algorithms, software, and processing that are little related to the invention and known by those of ordinary skill in the art are omitted.

Figure 1:
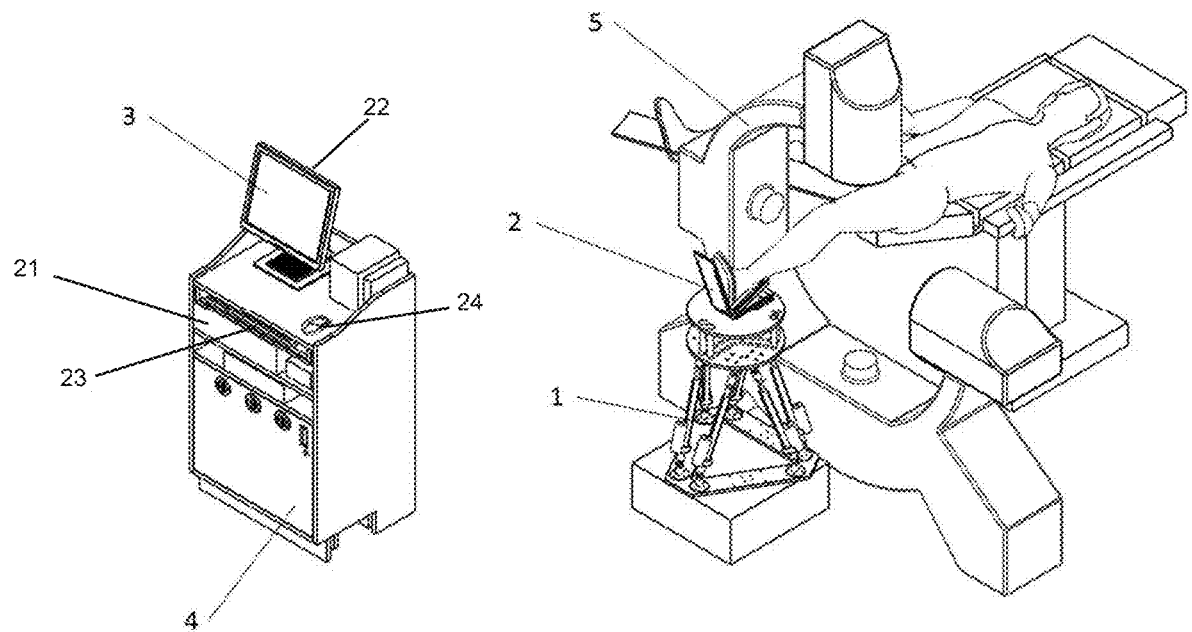
FIG. 1 is a perspective view of the robot system of the present invention in an operation room.

FIG. 1 is an illustration of the layout of the system proposed in the present application in an operating room. In this embodiment, 1 is a Stewart type parallel robot, 2 is a fixator for coupling the patient's foot to the end effector of the robot in a long bone fracture reduction surgery, 3 is the graphical user interface shown on the screen of the remote operation workstation 4, and 5 is a surgical image acquisition device that is a G arm X-ray machine in this embodiment. The surgical image acquisition device 5 is connected to the remote operation workstation 4 through a data line or a wireless network. The remote operation workstation 4 is connected to the fracture reduction robot 1 through a data line or a wireless network. The remote operation workstation 4 is equipped with visual servo control software for controlling the fracture reduction robot 1, artificial intelligence algorithm software for planning the fracture reduction path, and a graphical user interface 3. During the operation, the said surgical image acquisition device 5 acquires two real-time images, one from the AP view and the other from a LT view, which are sent to the remote operation workstation 4. The operator makes the fracture reduction path plan with the images displayed on the graphical user interface 3 and the workstation 4 calculates the control quantity and then sends instructions to the robot 1 according to the path planning results. The fracture reduction robot 1 then performs a movement according to the received control quantity.

The said surgical image acquisition device 5 can be any commonly used image acquisition device such as a C-arm or G-arm X-ray machine, which is used to acquire anteroposterior (AP) or lateral (LT) images of the fracture site.

Figure 2:
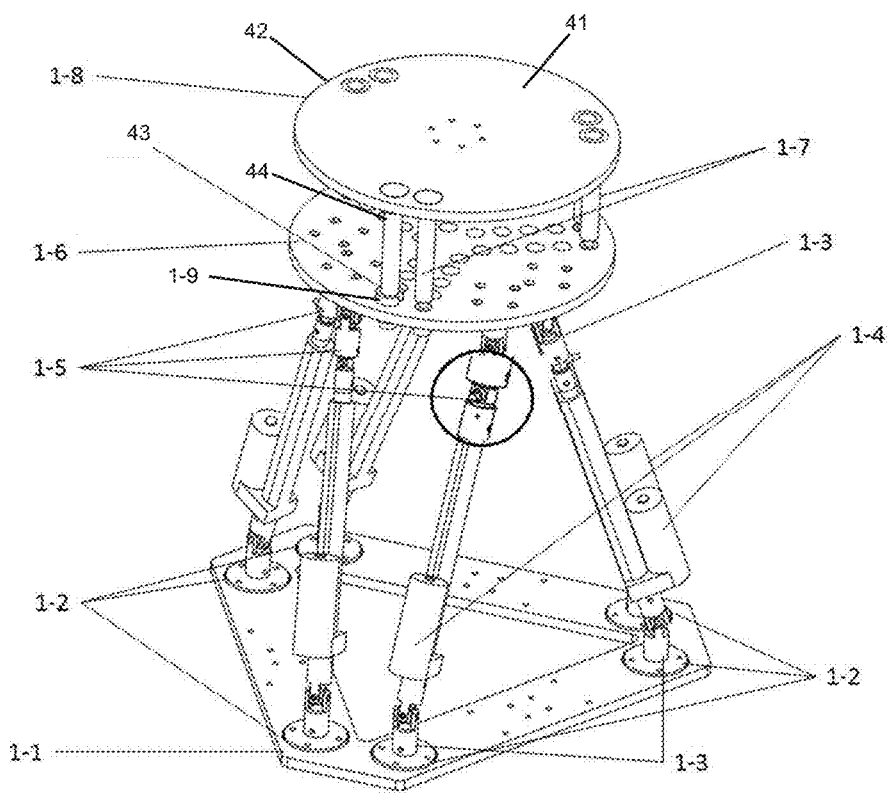
FIG. 2 is a perspective view of a Stewart type parallel robot provided by an embodiment of the invention.

The fracture reduction robot needs 6 degrees of freedom, but has no requirement on the specific type of robot to be used. In the embodiment of FIG. 1 a Stewart type parallel robot 1 is used to manipulate the fractured limb and perform the fracture reduction. Stewart type parallel robots have been widely applied to fracture reduction surgery (see, G. Lebret, K, Liu and F. L. Lewis, Dynamic Analysis and Control of a Stewart Platform Manipulator, Journal of Robotic Systems, 1993, Vol. 10, No. 6, pp. 629-655). FIG. 2 is a perspective diagram of the Stewart type parallel robot provided by this embodiment of the invention. In FIG. 2, 1-1 is the fixing platform for mounting the robot on a moving table such as a dolly, or a fixed table; 1-2 is the mounting plate for connecting the strut type actuator 1-4 to the fixing platform 1-1; 1-3 is the universal joint for realizing the feature of the Stewart type parallel robot; 1-5 is a single degree-of-freedom force sensor for measuring the force and force variation during the robot's movement; 1-6 is the end effector which is also called a platform. Different from conventional Stewart type parallel robots, in this embodiment, a disinfection work platform 1-8 is added and connected to the end effector 1-6 of the robot by a plurality of connecting columns 1-7 that are fixed to the two platforms by a plurality of snap rings 1-9 for easily assembling and disassembling the disinfection work platform 1-8.

The disinfection work platform 1-8 includes an upper surface 41 which is preferably substantially planar and rigid, in order to support the weight of a patient's leg or other appendage or body part which is placed thereon. The upper surface 41 preferably comprises a smooth surface in order facilitate cleaning and disinfection, and is formed from a material that can be cleaned and disinfected through the use of chemical disinfectants, heat, radiation, or other means for disinfecting the upper surface 41. In use, a sheet of clean and/or sterile material which is preferably disposable may be placed over the upper surface 41 of the disinfection work platform 1-8 in order to maintain a clean and/or sterile operating environment. In order to avoid injury to a patient, the periphery 42 of the disinfection work station 1-8 is preferably radiused or rounded. The disinfection work platform 1-8 is illustrated as being circular, but other configurations can also be used.

The lower surface of the disinfection work platform 1-8 is preferably connected to the end effector 1-6 in a spaced-apart manner such as through the use of connecting columns 1-7. The disinfection work platform 1-8 is preferably removably secured to the end effector by a plurality of connecting columns 1-7, with each connecting column 1-7 comprising a proximal end 43 removably secured to the end effector and a distal end 44 removably secured to the disinfection work platform 1-8.

FIG. 3(a) is a perspective diagram of a foot-fixing device or fixator 2 for coupling a patient's foot to the end-effector of the robot, which is the disinfection work platform 1-8 in this embodiment. In FIG. 3(a), 2-1 is the fixing base for connecting the foot-fixing device 2 to the disinfection work platform 1-8; 2-2 is the linkage for adjusting the inclination angle of L shaped brace 2-5; 2-3 is the bolt for fixing the linkage 2-2 in place; 2-4 is the sliding rail for connecting the L shaped brace 2-5, on which a clamp shoe for fixing the patient's foot is connected, to the fixing base 2-1 and removably securing the sliding rail 2-4 to the L shaped brace 2-5; 2-6 is the pin hole for fixing the L shaped brace 2-5 to the sliding rail 2-4. The linkage 2-2 has a proximal end and a distal end, with the proximal end attached to the fixing base 2-1 and the distal end attached to the sliding rail 2-4. The sliding rail 2-4 and the fixing base 2-1 are hingedly connected at a proximal end, while the distance between the distal ends of the sliding rail 2-4 and the fixing base 2-1 can be changed by moving the bolts 2-3 on either lateral side of the fixing base 2-1 from one a more proximal hole or receptacle to a more distal one, or vice-versa.

Figure 3:
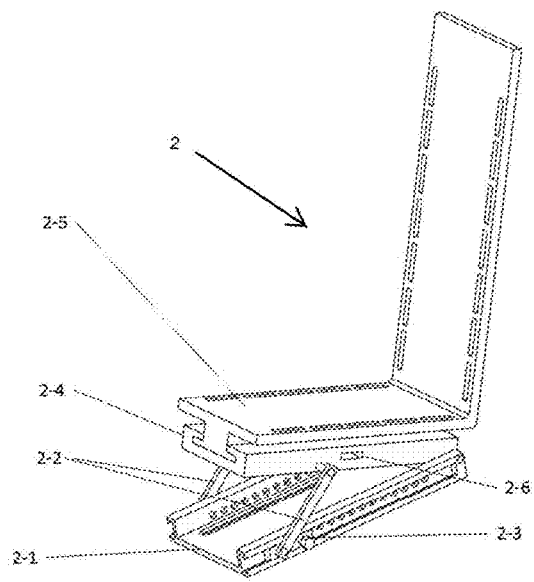
FIG. 3(a) is a perspective view of a foot-fixing device for coupling a patient's foot to the end-effector of a robot.
FIG. 3(b) is a perspective view of a foot-fixing device for coupling a patient's foot to the end-effector of a robot.
Figure 3:
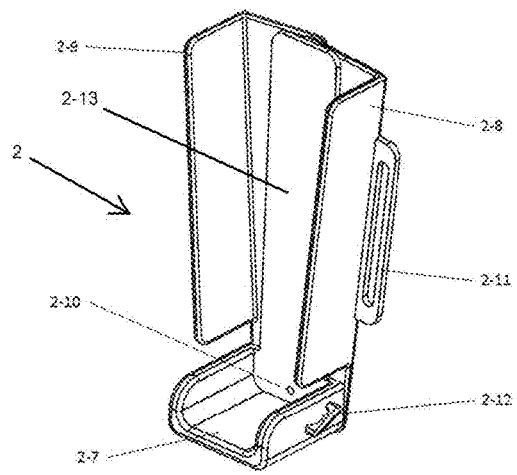

FIG. 3(b) is another perspective diagram of a foot-fixing device 2 for coupling the patients' foot to the end-effector of the robot, which is the disinfection work platform 1-8 in the illustrated embodiment. 2-7 is the bottom plate having an upper surface for supporting a patient's foot and a lower surface for attachment to the sliding rail 2-4 shown in FIG. 3(a). 2-8 and 2-9 provide side restriction to the foot, and they can rotate around the axis 2-10. Handle-like structures 2-11 and 2-12 are for fixing bandages being used for fixing the patient's foot to the device. 2-13 is a rigid plate secured at an angle, preferably a 90° angle, to the upper surface of the bottom plate 2-7 The L shaped brace formed by 2-7 and 2-13 is for supporting patient's foot and is connected to the sliding rail 2-4. Different from the device shown in FIG. 3(*a*), this device does not require a patient to wear a clamp shoe on their foot.

In use, the lower surface of the fixing base 2-1 is secured to the upper end of the end effector of the robot. The lower surface of the fixing base 2-1 is preferably removably secured to the upper surface 41 of the disinfection work platform 1-8 in the illustrated embodiments. Like the disinfection work platform 1-8, the foot-fixing device or fixator 2 preferably comprises smooth surfaces in order facilitate cleaning and disinfection, and is formed from a material that can be cleaned and disinfected through the use of chemical disinfectants, heat, radiation, or other means for disinfection.

In this embodiment, as shown in FIG. 1, a patient's foot of the limb having a fracture is fixed to the foot-fixing device 2 which is fixed on the disinfection work platform 1-8. For a tibia bone fracture, a clamp shoe with an upper higher than the patient's ankle joint is placed onto the patient's foot first, and then the clamp shoe is fixed on the L shape brace 2-5 by flexible ropes or flexible bandages. The inclination angle is adjusted to a proper value by moving the linkage 2-2 along the sliding rail 2-4. As is common knowledge, if the fracture bone is the femur, for protecting the ankle joint and the knee joint, a pair of splints should be fixed on the leg from the ankle joint to the knee joint with flexible bandages. To restrict the relative rotation around the knee joint, the splint preferably has a bending angle corresponding to the position of the knee and extends to the femur. Another way of doing this is to put a plate, which has a bending angle corresponding to the position of the knee, under the limb and fix it to the limb with flexible bandages. A preferred angle is 35 degrees. Although FIG. 1 only describes an embodiment for the lower limb, for upper limb fracture reduction, as is common knowledge, the hand should be tied to the robot's end effector with a flexible bandage, and if necessary, a pair of splints is installed between the wrist joint and the elbow joint with a flexible bandage.

Figure 5:
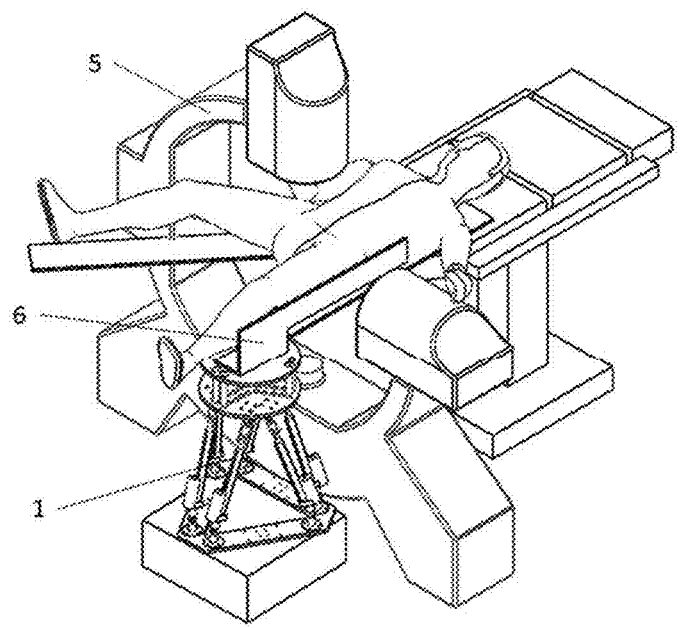
FIG. 5 is a perspective view of an embodiment of the invention with a Stewart type parallel robot for pelvis fracture reduction surgery.

FIG. 5 presents an embodiment for the fracture reduction of a pelvis, wherein a part of the pelvis is fixed on the surgical table, and the other part of the pelvis is fixed to the Stewart type robot's end effector by a plurality of metal pins. To expose the pelvis to X-rays, the space below the patient's pelvis should be left to the X-ray machine 5. Therefore, a plate 6, which is made from a material being transparent to X-ray, is used for fixing the fractured part of the pelvis to the robot's end effector 1-8.

Figure 6:
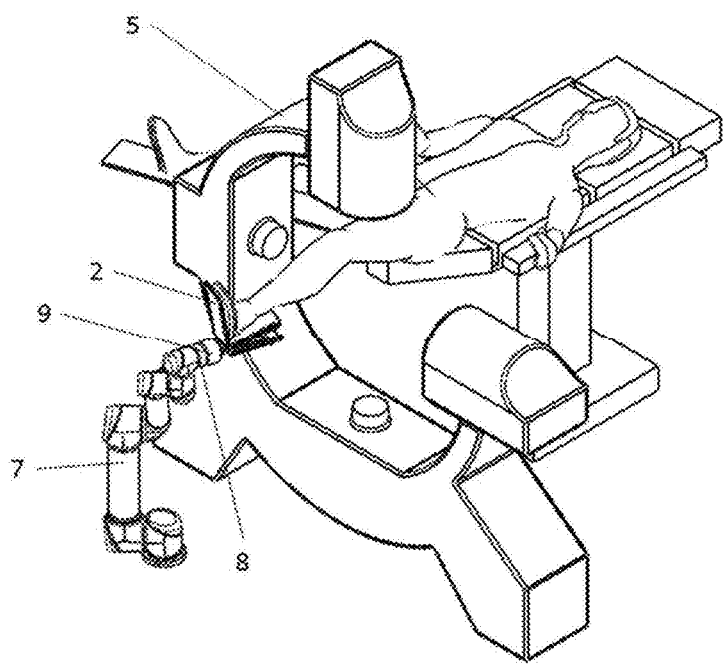
FIG. 6 is a perspective view of an embodiment of the invention with a serial robot as the fracture robot.

FIG. 6 presents an embodiment of the present invention using a serial robot 7, which can realize six degree-of-freedom motion of the foot-fixing device 2 and hence the patient's fractured bone. The foot-fixing device 2 is connected to the end effector 9 of the robot, and a six degree-of-freedom force sensor 8 is arranged between the end effector 9 and the arm of the robot 7.

Figure 7:
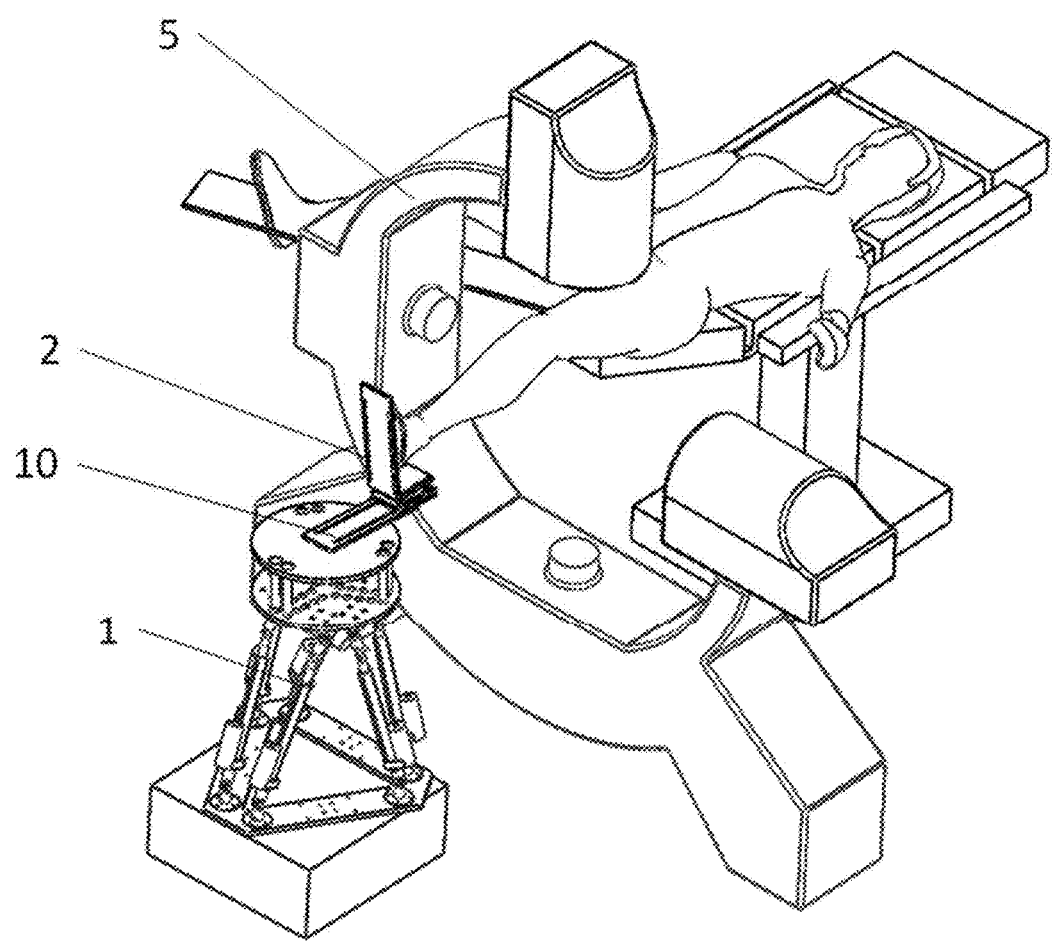
FIG. 7 is a perspective view of an embodiment of the invention with a Stewart type parallel robot for fracture reduction surgery of a shorter leg.

FIG. 7 presents a way of connecting the foot to the robot when the patient has a shorter leg that cannot leave enough space for arranging an X-ray machine. In this case, an extension beam 10 can be used to connect the foot-fixing device 2 shown in FIG. 3 to the disinfection work platform 1-8 of the robot. The extension beam 10 comprises a proximal end which is secured to the disinfection work platform 1-8, preferably by removably securing the proximal end of the extension beam 10 to the upper surface 41 of the disinfection work platform 1-8. The distal end of the extension beam 10 extends beyond the periphery 42 of the disinfection work platform 1-8, and the foot-fixing device 2 is secured to the distal end of the extension beam 10.

Figure 8:
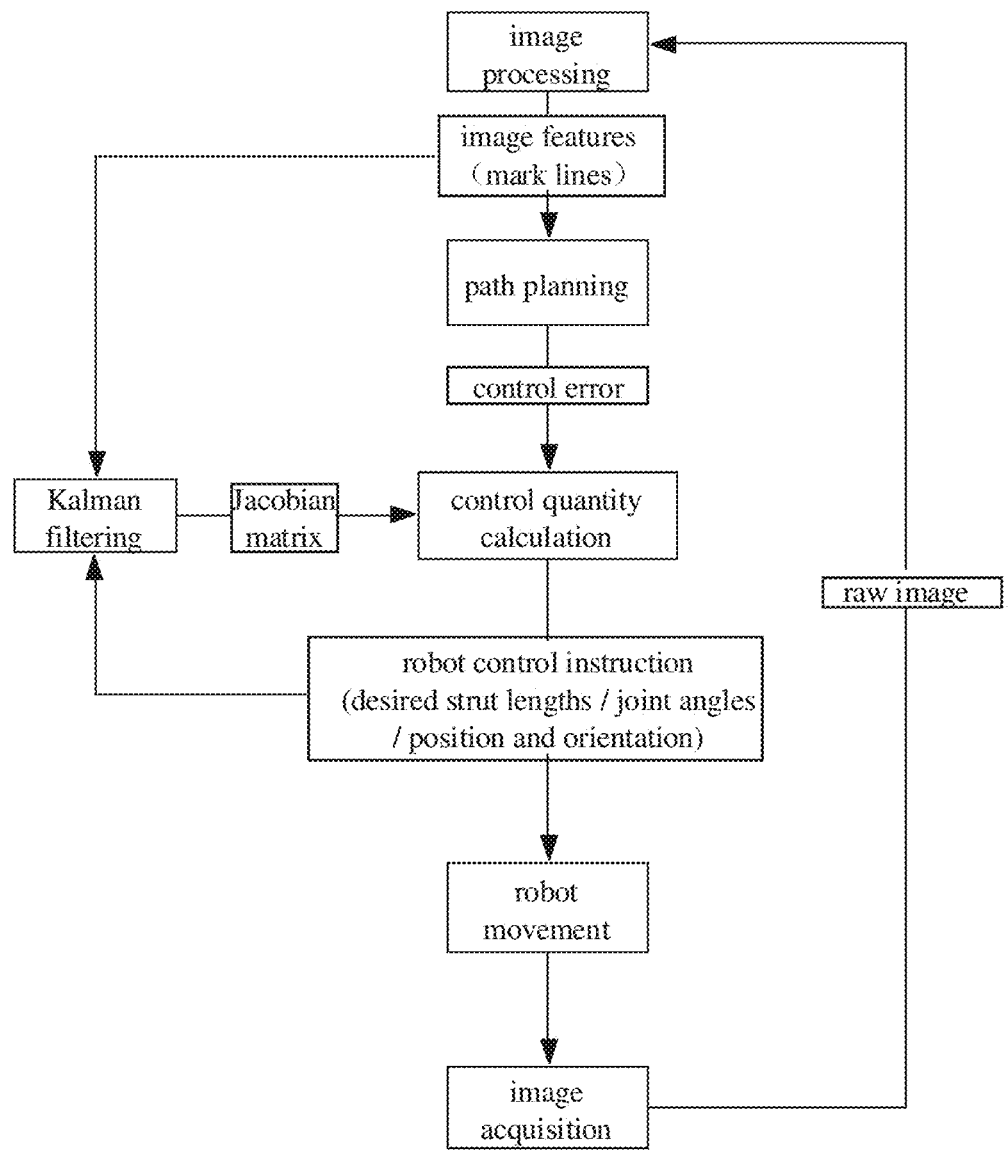
FIG. 8 is a flow chart of the visual servo control software.

FIG. 8 is the flow chart of the visual servo control software. The software is installed in the said remote operation workstation.

Figure 4:
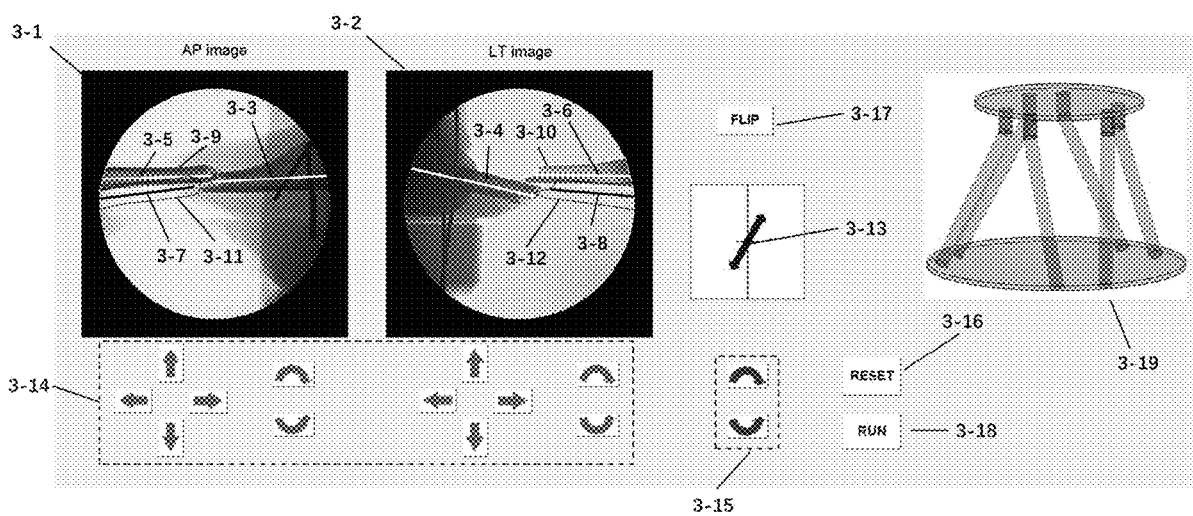
FIG. 4 is a diagram of a graphical user interface for fracture reduction in an embodiment of the invention which uses a Stewart type parallel robot.

As shown in FIG. 1, the said remote operation workstation 4 preferably comprises a workstation host 21, a display 22, a keyboard 23, and a mouse 24. The remote operation workstation is equipped with a graphical user interface 3 for fracture reduction path planning and a fracture reduction robot control program for robot control quantity calculation. A preferred embodiment of the graphical user interface for fracture reduction path planning installed on the remote operation workstation 4 is shown in FIG. 4, whose details and the fracture reduction control method, based on the visual servo control technology, are described as follows. The flow chart of the control method is shown in FIG. 8.

In the following description of the embodiment, the bone segment of the fractured limb that is fixed to the surgical table is called the proximal bone segment, and the bone segment of the fractured limb that is fixed to the robot manipulator is called the distal bone segment.

1) Considering the requirements of fracture reduction, we use a G-arm X-ray machine 5 in this embodiment (or a C-arm X-ray machine acquiring images from perpendicular directions). The images acquired by the G-arm X-ray machine are displayed on the X-ray image display areas 3-1 and 3-2 on the graphical user interface 3 to display AP image and LT image respectively.

2) The path planning related mark lines, contours and arrows are displayed on the corresponding position in each fluoroscopy image. The graphical user interface for fracture reduction path planning in the embodiment described in FIG. 1 is shown in FIG. 4. The graphical user interface displays at least the following path planning related mark lines and contours: mark lines representing the midline of the proximal bone segment 3-3 and 3-4, mark lines representing the midline of the distal bone segment 3-5 and 3-6, mark lines representing the midline of the distal bone segment after the robot movement 3-7 and 3-8, contour lines of the distal bone segment 3-9 and 3-10, contour lines of the distal bone segment after the robot movement 3-11 and 3-12, and an indicator representing the rotation angle of the axis of the distal bone segment after the robot movement 3-13 (shown as a double arrow in FIG. 4). Preferably, the path planning related mark lines and contours are shown by overlaying them or incorporating them into the fluoroscopy images, as shown in 3-1 and 3-2.

3) The remote operation workstation 4 further includes controls used for manual fracture reduction path planning. These can be touch controls or controls operated by a pointing device such as a mouse which are incorporated into the graphical user interface as shown in FIG. 4, or can be controls in a separate physical control unit. As shown in FIG. 4, the controls preferably include six buttons (shown as arrows) 3-14 under or otherwise associated with both the AP and LT image display areas, representing movement upward, movement downward, movement to the left, movement to the right, clockwise rotation, and counterclockwise rotation, respectively. When these buttons are activated (such as by touching or pressing them), the said mark lines representing the midline of the distal bone segment 3-5 and 3-6, and the contour lines of the distal bone segment 3-9 and 3-10, will translate and/or rotate correspondingly. The buttons also include two buttons 3-15 representing "rotate clockwise" and "rotate counter clockwise". When these two buttons are pressed, the double arrow representing the rotation angle of the axis of the distal bone segment after the robot movement 3-13 will rotate correspondingly.

4) When the buttons used for path planning are pressed, the state of the parallel robot shown in 3-19 also changes accordingly. In the embodiment as shown in FIG. 1, if the strut type actuators 1-4 exceed their travel limitations or the universal joints 1-3 exceed their angle limitations, the color of the strut type actuators 1-4 or the joints 1-3 in the graphical user interface (as shown in FIG. 4) will change correspondingly. For the serial robot shown in FIG. 6, if any joint of the robot 7 exceeds its angle limitation, the color of this joint will change accordingly.

5) The graphical user interface further preferably includes a reset control. When the reset button is activated, the path planning related mark lines, contours and arrows will go back to their original positions, that is, the mark lines representing the midline of the distal bone segment after the robot movement 3-7 and 3-8 will go back to where the mark lines representing the midline of distal bone segment 3-5 and 3-6 are; the contour lines of the distal bone segment after the robot movement 3-11 and 3-12 go back to where the contour lines of the distal bone segment 3-9 and 3-10 are; the double arrow representing the rotation angle of the axis of the distal bone segment after the robot movement 3-13 goes back to a vertical orientation.

6) The graphical user interface further preferably includes a "flip" control. When the flip button 3-17 is pressed, the mark lines representing the midline of the distal bone segment 3-5 and 3-6 will swap positions with the mark lines representing the midline of proximal bone segment; the existing contour lines 3-9 and 3-10 will be deleted, the contour lines of the other bone segment will be shown, and this bone segment will now be referred to as the distal bone segment. This function is for the case that the image processing algorithm mistakenly takes the distal bone segment as the proximal bone segment or takes the proximal bone segment as the distal bone segment.

7) The graphical user interface further preferably includes a "run" control. When the run button 3-18 is pressed, the workstation 4 calculates the control error e as follows and sends this control error to the robot control program to calculate the robot control quantity. Let $\Delta x_1$, $\Delta y_1$ and $\Delta \theta_1$ be the horizontal displacement, the vertical displacement and the rotation angle of "the contour line of the distal bone segment after the robot movement" and "the mark line representing the midline of the distal bone segment after the robot movement" generated by the doctor's operation in the AP fluoroscopy image through the graphical user interface. Let $\Delta x_2$, $\Delta y_2$, $\Delta \theta_2$ be the horizontal displacement, the vertical displacement and the rotation angle of "the contour line of the distal bone segment after robot movement" and "the mark line representing the midline of the distal bone segment after robot movement" generated by the doctor's operation in the LT fluoroscopy image through the graphical user interface. Let $\alpha$ be the angle between the vertical direction and "the double arrow representing the rotation angle of the axis of the distal bone segment after the robot movement". Thus the control error e is given by $$e = [\Delta x_1 \, \Delta y_1 \, \Delta \theta_1 \, \Delta x_2 \, \Delta y_2 \, \Delta \theta_2 \, \alpha]^T$$

The above graphical user interface can be realized by a person skilled in this field.

8) With the control error e, according to the "image-based calibration-free visual servo" control law, the control quantity r can be give as:

$$r = J^\dagger \left( -k_p e - k_1 \int e \, dt - k_d \frac{de}{dt} \right)$$

Wherein r is a vector representing the length variation of the six strut type actuators of the Stewart platform; $k_P$, $k_I$, $k_D$ are the proportional coefficient, integral coefficient and differential coefficient respectively; J is the Jacobian matrix acquired by the Kalman filtering the image features (mark lines of the bone fragments) and the robot control instructions, which establishes a relationship between changes in fluoroscopy images and motions of the fracture reduction robot is the integration of control error e over time t, $$\frac{de}{dt}$$

is the derivative of the control error e to time t. Then let the robot move according to the control quantity r. Let l be the vector representing the current lengths of the six strut type actuators of the Stewart platform, then the desired lengths of the strut type actuators (the control instructions) are l+r, which are sent to the Stewart platform and it moves accordingly.

To calculate the reduction error w, in the AP fluoroscopy image, let the angle between the horizontal direction and the mark line, which represents the midline of proximal bone segment, be $\theta_1$, and the pixel coordinates of its endpoint close to the side of the fractured segment be $(x_1, y_1)$, the angle between the horizontal direction and the mark line, which represents the midline of the distal bone segment, be $\hat{\theta}_1$, and the pixel coordinates of its endpoint close to the side of the fractured segment be $(\hat{x}_1, \hat{y}_1)$. In the LT fluoroscopy image, let the angle between the horizontal direction and the mark line, which represents the midline of the proximal bone segment, be $\theta_2$, and the pixel coordinates of its endpoint close to the side of the fractured segment be $(x_2, y_2)$, the angle between the horizontal direction and the mark line, which represents the midline of distal bone segment, be $\hat{\theta}_2$, and the pixel coordinates of its endpoint close to the side of the fractured segment be $(\hat{x}_2, \hat{y}_2)$. With these definitions, the reduction error w is given by $$w = \begin{bmatrix} \hat{x}_1 - x_1 \\ \hat{y}_1 - y_1 \\ \hat{\theta}_1 - \theta_1 \\ \hat{x}_2 - x_2 \\ \hat{y}_2 - y_2 \\ \hat{\theta}_2 - \theta_2 \end{bmatrix}$$

If $\|w\| \geq \varepsilon$ then system will acquire new fluoroscopic images; if $\|w\| < \varepsilon$ then the image acquisition loop is stopped and the fracture reduction operation is finished. The said $\varepsilon$ is a predefined threshold according to the surgery requirement.

Figure 9:
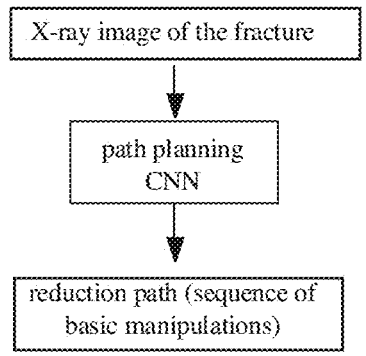
FIG. 9 is a flow chart of an AI method applying a convolutional neural network (CNN) for fracture reduction path planning.

As shown in FIG. 9, the artificial intelligence (AI) path planning algorithm is a convolutional neural network (CNN) (as described in Goodfellow et al., Deep Learning, MIT Press, 2016), whose input is the X-ray image of the fracture and the output is the reduction path, which is represented by a sequence of basic manipulations including traction, bending, rotation or the combination of these.

Figure 10:
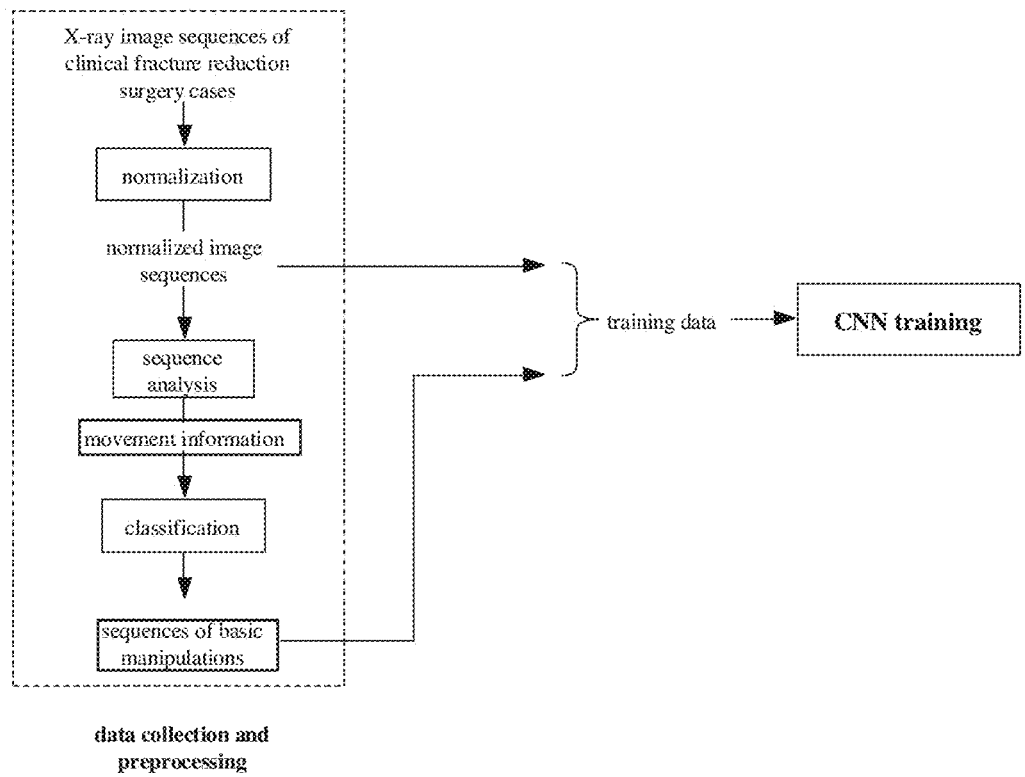
FIG. 10 is a diagram illustrating a procedure for collecting and preprocessing the data for training the convolutional neural network (CNN).

To apply AI technology for use in the present system, the CNN algorithm is trained with data. The data collection and preprocessing process is shown in FIG. 10, and preferably includes:

1) collecting the X-ray image sequences of clinical fracture reduction surgery cases such that every image sequence records a complete process of a fracture reduction;

2) normalizing these image sequences, including size normalization and grayscale normalization;

3) analyzing the difference between the adjacent images in the sequence to extract the movement information from the image sequence;

4) classifying these movements into several basic manipulations, including traction, bending, rotation or the combination of them, in this way the reduction process of each image sequence is described as a sequence of basic manipulations.

The training data is the normalized image sequences and the corresponding sequence of basic manipulations of the above-described step 2) and step 4), respectively.

What is claimed is:

1. A remotely operated orthopedic surgical robot system for fracture reduction surgery comprising a visual-servo control system, wherein the orthopedic surgical robot system does not have position sensors, trackers or markers, comprising:
    surgical image acquisition equipment capable of taking two orthogonal fluoroscopy images;
    a fracture reduction robot capable of realizing at least six degree-of-freedom spatial motion and having an end effector that can be coupled to a foot-fixing device, wherein the fracture reduction robot is a parallel robot or a serial robot;
    visual servo control software for establishing a relationship between changes in fluoroscopy images and motions of the fracture reduction robot, wherein the visual servo control software generates control instructions for controlling the robot's motions;
    software for planning a fracture reduction path, wherein the software comprises an artificial intelligence algorithm;
    a graphic user interface for displaying the fluoroscopy images, exhibiting a fracture reduction path planned by the software for planning a fracture reduction path, and providing operation controls for examining, verifying and/or modifying the fracture reduction path planned by the software for planning a fracture reduction path; and
    a remote operation workstation in communication with the fracture reduction robot and the surgical image acquisition equipment through data lines and/or a wireless network.

2. The orthopedic surgical robot system of claim 1, wherein the surgical image acquisition equipment is a G arm X-ray machine or a C arm X-ray machine.

3. The orthopedic surgical robot system of claim 2, wherein the C arm X-ray machine has the ability to collect two orthogonal X-ray images.

4. The orthopedic surgical robot system of claim 1, wherein the fracture reduction robot is a Stewart type parallel robot or a robot having a manipulator with multiple joints in series.

5. The orthopedic surgical robot system of claim 4, comprising a serial robot having a manipulator with multiple joints in series, wherein a six degree-of-freedom force sensor is installed between the end effector and a disinfection work platform.

6. The orthopedic surgical robot system of claim 1, wherein the foot fixing device is connected to a disinfection work platform by an extension beam.

7. The orthopedic surgical robot system of claim 1, wherein the foot-fixing device comprises an L shaped brace having an adjustable inclination angle.

8. The orthopedic surgical robot system of claim 1, wherein the software for planning a fracture reduction path comprises an artificial intelligence algorithm based on a deep learning method with a convolutional neural network trained by data collected from fracture reduction surgeries.

9. A fracture reduction method performed with an orthopedic surgical robot system, comprising the steps of:
    (a) providing an orthopedic surgical robot system which comprises:
        (i) surgical image acquisition equipment capable of taking two orthogonal fluoroscopy images,
        (ii) a fracture reduction robot capable of realizing at least six degree-of-freedom spatial motion and having an end effector that can be coupled to a foot-fixing device,
        (iii) visual servo control software for establishing a relationship between changes in fluoroscopy images and motions of the fracture reduction robot,
        (iv) software for planning a fracture reduction path,
        (v) a graphic user interface for displaying the fluoroscopy images, exhibiting a fracture reduction path, and providing operation controls for examining, verifying and/or modifying the fracture reduction path, and
        (vi) a remote operation workstation in communication with the fracture reduction robot and the surgical image acquisition equipment through data lines and/or a wireless network;
    (b) coupling a subject's fractured limb to the end effector of the fracture reduction robot;
    (c) collecting one anteroposterior (AP) fluoroscopy image and one lateral (LT) fluoroscopy image of a fractured bone of a subject with the surgical image acquisition equipment and sending the images to the remote operation workstation through the data line or the wireless network;
    (d) presenting the collected AP and LT fluoroscopy images to an operator with the graphic user interface;
    (e) planning a fracture reduction path for the fractured bone;
    (f) determining whether fracture reduction should be continued by determining when an absolute value of a reduction error value is less than a predetermined value;
    (g) if the reduction error value is less than the predetermined value, stopping the fracture reduction process, or if the reduction error value is greater than the predetermined value, calculating a control error value with the visual servo control software;
    (h) calculating robot control quantities with the control error together with the visual servo control software utilizing change history of predetermined features of the images and change history of the robot control quantities, without using computed tomography (CT) image data and/or infrared optical navigation data and also without arranging markers on the subject's body;
    (i) sending the calculated robot control quantities to the fracture reduction robot and moving the fracture reduction robot according to the robot control quantities; and
    (j) after moving the fracture robot, collecting new AP and LT fluoroscopy images with the surgical image acquisition equipment and sending the new AP and LT fluoroscopy images to the remote operation workstation for the operator to examine the reduction result.

10. The method of claim 9, wherein the control error value $e=[\Delta x_1\ \Delta y_1\ \Delta \theta_1\ \Delta x_2\ \Delta y_2\ \Delta \theta_2\ \alpha]^T$, wherein $\Delta x_1$, $\Delta y_1$, $\Delta \theta_1$ are the horizontal displacement, the vertical displacement, and the rotation angle of a contour line of a distal bone segment of the subject after the fracture reduction robot is moved with respect to a first mark line, which represents a first midline of the distal bone segment after the fracture reduction robot's movement in the AP fluoroscopy image generated using the graphical user interface;

wherein $\Delta x_2$, $\Delta y_2$, $\Delta \theta_2$ are the horizontal displacement, the vertical displacement and the rotation angle of the contour line of the distal bone segment after the fracture reduction robot's movement with respect to a second mark line, which represents a second midline of the distal bone segment after the robot's movement in the LT fluoroscopy image generated using the graphical user interface; and wherein $\alpha$ represents the angle of a double arrow, which represents the rotation angle of the axis of the distal bone segment after the fracture reduction robot's movement with respect to the vertical direction;

further comprising the steps of:

calculating a robot control quantity r using the following formula:

$$r = J^\dagger \left( -k_p e - k_I \int e\, dt - k_d \frac{de}{dt} \right)$$

wherein the robot control quantity r is a vector representing the variation of the position and orientation of the robot end effector, or the robot control quantity r is a vector representing the variation of the lengths of the linear actuators or the angles of the joints of the robot; $k_P$, $k_I$, $k_D$ are the proportional coefficient, integral coefficient and differential coefficient respectively; J is the image Jacobian matrix; $\int e\, dt$ is the integration of control error e over time t, $$\frac{de}{dt}$$

is the derivative of the control error e to time t; and sending the robot control quantity r to the fracture reduction robot.

11. The method of claim 9, wherein the reduction error value is a vector that describes the relative position of a proximal end and a distal end of the fractured bone, and the reduction error value is the difference between pixel coordinates of a corresponding point and an angle between the first midline or the second midline of the distal bone segment and a fixed fractured bone segment.

12. The method of claim 11, wherein the ideal fracture reduction error value is 0.

13. The method of claim 9, comprising the steps of:

installing force sensors between the fracture reduction robot's end effector and a fixator of an injured body part of the subject, and measuring the force change rate to determine whether there is any contact between the fractured segments of the subject's bone.

14. The fracture reduction method of claim 9, wherein the subject has a tibia fracture and the patient's foot is fixed on the foot-fixing device.

15. The fracture reduction method of claim 9, wherein the subject has a femur fracture, wherein the subject's foot is fixed on the food-fixing device, and wherein a pair of splints or a single plate is fixed on the leg from the ankle joint to the knee joint with flexible bandages, the splint or the plate has a bending angle at the position of knee.

16. The fracture reduction method of claim 9, wherein the subject has an upper limb fracture and a hand of the subject is tied to the robot's end effector with a flexible bandage, and wherein a pair of splints is optionally installed between the wrist joint and the elbow joint with a flexible bandage.

17. The fracture reduction method of claim 9, wherein the subject has a pelvic fracture, wherein a first a part of the pelvis is fixed on a surgical table, and wherein a second part of the pelvis is fixed to the fracture reduction robot's end effector by a plurality of metal pins.

18. The fracture reduction method of claim 17, wherein the second part of the fractured pelvis is coupled to the fracture reduction robot's end effector by a plate or a frame that is made from a material transparent to X-rays.

19. A parallel robot for use with orthopedic procedures, comprising:

a fixing platform for mounting the robot on a surface;

an end effector for mounting a disinfection work platform;

a plurality of strut type actuators, each actuator having a proximal end and a distal end, the proximal end being attached to the end effector with a universal joint, and the distal end being attached to the fixing platform with a universal joint;

the disinfection work platform, wherein the disinfection work platform is attached to the end effector in a spaced-apart manner, wherein the disinfection work platform is removably secured to the end effector by a plurality of connecting columns, each connecting column comprising a proximal end and a distal end, and wherein the proximal end of each connecting column is removably secured to the end effector and the distal end of each connecting column is removably secured to the disinfection work platform;

a force sensor installed between the proximal end of the actuator and the end effector;

snap rings securing the connecting columns to the end effector; and a foot-fixing device which is removably secured to the upper surface of the work platform.

20. The parallel robot of claim 19, wherein the force sensor measures force and force variation rate at the same time, and when the force exceeds a specified amplitude or the force variation rate raises abruptly, the robot activates an alarm and stops motion automatically.

* * * * *